United States Patent [19]

Heck et al.

[11] Patent Number: 4,940,056
[45] Date of Patent: Jul. 10, 1990

[54] ELECTROGUSTOGRAPH

[75] Inventors: Gerard L. Heck; John A. DeSimone, both of Richmond, Va.

[73] Assignee: Center for Innovative Technology, Herndon, Va.

[21] Appl. No.: 271,317

[22] Filed: Nov. 15, 1988

[51] Int. Cl.$^5$ ................................................ A61B 5/04
[52] U.S. Cl. .................................... 128/639; 128/734; 604/289
[58] Field of Search .............. 128/734, 639, 643, 777, 128/642, 66, 400; 604/31, 50, 66, 77, 289, 290

[56] References Cited

U.S. PATENT DOCUMENTS

| | | | |
|---|---|---|---|
| 1,251,258 | 12/1917 | Magill | 128/334 R |
| 4,376,437 | 3/1983 | Sundheim et al. | 128/847 |
| 4,646,747 | 3/1987 | Lundback | 128/643 |

Primary Examiner—Lee S. Cohen
Assistant Examiner—Scott M. Getzow
Attorney, Agent, or Firm—Staas & Halsey

[57] ABSTRACT

The invention discloses an electrogustograph for detecting the physiological responses of the tongue to various tastants applied thereto through a small vacuum sensor. The small sensor has a peripheral annual vacuum port by which the sensor is attached to the top surface of the tongue. The annular vacuum port surrounds a cavity which has one port for insertion of the tastant which flows across the surface of a portion of the tongue to a second port which serves as an outlet for the tastant. Electrodes are present in the sensor and on the cheek of the person being tested so as to measure the difference in the flow of electricity across the top surface of the tongue when various tastants are applied to the tongue. The electrogustograph is supported by suitable electronics and fluid flow pumps and valves all under the control of a microcontroller to provide a flexible and relatively easy to use electrogustographic system.

15 Claims, 10 Drawing Sheets

VOLTAGE AND RESISTANCE CHANGES OF HUMAN TONGUE TO NaCl STIMULATION

EFFECT OF 60 μM CPC ON THE VOLTAGE RESPONSE OF THE HUMAN TONGUE TO NaCl

VOLTAGE AND RESISTANCE CHANGES OF HUMAN TONGUE TO KCl STIMULATION

VOLTAGE AND RESISTANCE CHANGES OF HUMAN TONGUE TO HCl STIMULATION

ELECTROGUSTOGRAPH

This invention relates to an apparatus for measuring physiological responses to chemical stimulation and especially the electrical response to stimulation of the taste buds of the tongue by various chemicals such as table salt.

It has been a long felt need for an electrogustograph (EGG) to assist in research into the sense of taste as well as for diagnostic purposes, screening of food products, quality control of food taste and similar purposes. A specific need is for the electrogustograph to evaluate the relationships of the transepithelial electrical responses of the tongue while simultaneously evoking peripheral neural responses to chemical stimulation. This has been done by the present invention which shows a distinct correspondence between the rate of adaptation of the neural response to the rate of change of the transepithelial electrical responses and thus the electrogustograph measures events intimately connected with the chemotransduction process.

Various methods have been used to present taste stimuli to the tongue in the past. A 1941 pioneering study applied the solutions by brush. While effective, this technique had a disadvantage of exciting tactile as well as chemosensory responses. In 1953, a transparent plastic flow chamber which can fit over the anterior portion of a test animal's tongue was utilized. This allowed for a well defined rate of stimulus presentation, defined adapting conditions, and defined area of presentation of tastant. Since then a variety of chambers have been used, each modified to suit a particular need.

In 1971, animals studies were conducted where an animal tongue was extended from the mouth and fixed to a small plastic platform by a dissecting pin through the contralateral side of the tongue. A bilateral section of the hypoglossal nerves was performed to ensure the immobility of the tongue. A dilute methylene blue solution was applied to the tongue surface to individual fungiform papillae so that individual fungiform papillae could be easily identified under the magnification of a dissecting microscope.

Potentials from the nerve fibers were amplified by a preamplifier, the output of which was simultaneously displayed on a oscilloscope and recorded on magnetic tape. Subsequently, the action potentials were played back through the oscilloscope and photographed.

A single papilla stimulator was used which consisted of two concentric tubes applied to the tongue. The outer tube was 1.6 mm in outside diameter. The inner tube was 0.5 mm in diameter with an annular space between the two tubes of 0.1 mm in width. A vacuum source with a fluid trap was applied to this annular chamber with vacuum being between 0.05 and 0.1 atmosphere of negative pressure. The central chamber of the stimulator, which is the inside diameter of the smaller of the two concentric tubes, is placed over a single papilla. The papilla is isolated from a stimulus solution applied over the part of the tongue surrounding the stimulator and likewise any solution introduced in the stimulator did not leak onto nearby papilla outside the circumference of the stimulator. Disposable syringes were used to insert the different stimuli solutions or distilled water rinse into the inner tube of the stimulator. This insertion pressure causes the liquid to flow into the stimulator chamber onto the tongue and exit thereof adjacent the papilla where it flows into the annulus chamber where it is evacuated by the vacuum which also sucks the stimulator to the surface of the tongue (*The Journal of General Physiology*, Vol. 57, 1971, Inglis J. Miller, Jr., pp. 1-25, "Peripheral Interactions Among Single Papillae Inputs to Gustatory Nerve Fibers").

In 1975, a chamber which allowed for the delivery of stimuli with defined average and which contained electrodes for passing current was utilized. These were used to stimulate the taste nerves electrically. In 1977, a chamber which included a conductivity monitor which served as a salt stimulus marker at the surface of the tongue was utilized. Stimulus flow was controlled so that microliter volumes could be delivered within a second. Specialized flow chambers has also been used in human psychophysical studies.

In 1972, a transparent plastic chamber into which a human tongue could be placed was used. Tastant solutions could be flowed tangently over the tongue surface. Over 90% of the tongue could be stimulated and the chamber was well suited to investigate the effect of flow rate on perceived taste intensity. This chamber Was modified in 1973 to study the effect of pulsatile flow on the perceived taste of table salt.

The present invention uses a stimulator which is part of a system which has provided the first recording of an electrogustograph (EGG) in humans. The present system minimizes awkwardness and discomfort associated with the procedure of testing various tastants and recording electrical changes across the surface of the tongue evoked by the tastants. Also, the present invention has demonstrated that sufficiently stable lingual potentials and currents can be measured with voltage reference and current sinking electrodes outside of the oral cavity. The design is sufficiently versatile and powerful to be attractive to researchers in chemoreception and as well provides a diagnostic instrument and instrument that can be used for quality control, and a research and development tool for the food industry with additional uses beyond chemoreception. The possibility exists that it can detect changes in lingual ion transport that may be secondary to conditions effecting the lower gastrointestinal tract and kidneys. The present invention has already been utilized in confirming a salt taste enhancer invention by the same inventors.

The tongue develops a potential difference that crosses the surface when taste stimuli are applied. This potential, or alternatively the current under voltage clamp, correlates with the evoked activity in the taste nerves and conveys similar information. This recorded current or potential will be referred to as an electrogustogram (EGG) and apparatus for producing it as an electrogustograph (EGG). These terms should not, however, be confused with "electro-gustometry" (the method by which electric current can be used as a stimulus to invoke a taste response). In the present case, the stimuli are standard chemicals or various test fluids and the response is normally electrical.

The present invention provides a noninvasive apparatus and system and method for measuring these electrical parameters. Such measurements will facilitate the development of a useful, predictive model of human taste transduction. The EGG has been developed from research examining the ion transport properties of the canine and rat dorsal lingual mucosa by the present inventors who have established that the lingual epithelium activity absorbs sodium and secretes chloride. One of the unique aspects of sodium absorption by the lingual epitheleum is the concentration range at which it occurs, extending well into the hyperosmotic range. This pathway can be blocked by inhibiting the basolateral sodium pumps with ouabain. Amiloride, the apical membrane sodium channel blocker also significantly inhibits the inward flux of sodium.

The stimulus evoked transepithelial electrical response is characteristic of the lingual response in vivo and the transepithelial electrical potential (or current) time course correlates with that of the neural response. The EGG records the tongue's electrical responses under stimulation in vivo. The Egg may consider conductance as well as potential or current as part of the overall EGG. While salt stimuli has primarily been used, acids and sugars evoke similar correlations. The bitter taste has not yet been investigated but it is assumed that it will likewise have similar correlated responses. Pharmacological dissection methods may be used in Egg protocols. For example, information passing down salt sensitive nerve fibers can be blocked using amiloride and this would not effect other submodalities such as bitter acid or sweet. Similarly, gymnemic acid may be used to block the sweet response. Under short circuit conditions, a sodium chloride stimulus evokes an initial fast inward current and conductance increase followed by a slow inward current and a slow conductance increase. These current and conductance changes coincide respectively with the rising phase and the adaptation phase of the neural response. The slow phase current rises to its asymptote with approximately the same time course as neural adaptation.

The EGG has additional advantages over those cited above since it allows noninvasive measurement of an agent's effect on the ion transport system which may be representative of the agent's effect on less accessible ion transport systems. The EGG may represent an effective convenient pharmacologic screen tool and can provide clinical aid in diagnosing dysgeusia and ageusia. It fills a need for a means of ascertaining normal functioning at the receptor organ level of taste, independent of the integrity of the rest of the system.

The EGG is designed to meet a number of general requirements. It must operate as a precision stimulator of the tongue. The sensor chamber must isolate a well defined area of the tongue for the stimulation. Placement of stimulus input and exit ports in the chamber are optimized hydrodynamically with the aim of obtaining reproducible stimulus flow across the surface of the tongue. The stimulus is applied as a flowing stream rather than a statically applied layer of tastant; this maximizes tastant access to receptor cells by minimizing unstirred layers at the surface of the tongue. The design ensures accuracy within 1% and allows variation in the concentration range over at least two orders of magnitude. Cross contamination between stimuli is controlled by the use of Teflon ® as far as possible in fluid delivery lines and by the system having the capability of flushing and purging critical fluid lines prior to their use.

The EGG is versatile when used in taste psychophysics. It is not the purpose of the EGG to replace psychophysics as an experimental or clinical tool but rather to extend it. The physiological measurements made by the EGG aids in distinguishing between central and peripheral mechanisms for various taste phenomenon, or between central and peripheral loci for lesions and taste deficits. The precise control of stimulation made possible by the invention results in lessening variability in psychophysical measurements. Furthermore, different protocols are more directly comparable. Because of the miniature size of the sensor chamber, the design is usable with psychophysical protocols which stimulate different sides of the tongue with different solutions. Of course, two different chambers can be integrated into a dual sensor chamber if this is desired. This technique is used either for discrimination between the two stimuli or for simultaneous presentation of psychophysical standard along with a stimulus for magnitude estimation.

The increased automation allows for efficient implementation of more complex protocols. The EGG automatically compensates for a systems specific parameters such as pump slewing rates, stimulus delays due to delivery tube length, differential voltage compensation for solution and tissues IR drops, electrode offsets, and numerous other bookkeeping details which otherwise complicate experimental protocols. The system permits preprogramed protocols for detection and recognition thresholds, difference limens under standard adaptation states, as well magnitude estimation curves spanning standard concentration ranges.

While the current EGG design is to provide a flexible system, it is to be recognized that when only a specialized use is desired the system can be simplified and customized for that specialized use.

A key to the present invention is the use of a chamber designed for controlled stimulation of the dorsal tongue while maintaining the area under stimulation in either current clamp or voltage clamp. This has significant physiological importance which will become clear as the invention is described in further detail.

The best known molecular theory of taste receptor function assumes that all tastants are absorbed through specific macromolecular receptors located in the microvilli of the taste bud cells. According to this theory, tastants equilibrate with receptors such that the fraction of sites occupied for a given concentration of tastant is given by a Langmuir adsorption isotherm. The neural output is hypothesized to be proportional to the fraction of total adsorption sites occupied. This relationship has proven descriptive of the taste response in many studies, and is an established basis for describing the taste response.

Use of this theory in a transduction model requires a coupling mechanism between the receptor site activation and receptor cell depolarization. The sites of ionic conductance change had been assumed to be exclusively on the basolateral membrane of the receptor cell. Further, the keratinized epithelial layer was deemed to be impermeable to both ionic and non-ionic substances. Among the candidates for such a mechanism are "second messenger" chemical intermediates such as the cyclic nucleotides, cell membrane surface pressure changes, and surface potential changes. Common to all of these is a final gating of ionic conductances leading to receptor cell depolarization.

However, the inventors have shown that not only is the dorsal tongue epithelium permeable to electrolytes, but also it is engaged in actively transporting some of these electrolytes. The ionic fluxes can be observed across the epithelium under stimulations and these fluxes have concentration dependencies which parallel taste responses and allow adsorption theory to be used in a transduction model with direct coupling of receptor site activation with receptor cell depolarization. The epithelial transport studies demonstrate existence of amiloride sensitive apical sodium channel responsible for the bulk of the sodium transport across the tissue for hyperosmatic sodium concentrations.

The phenomenological correlation of the EGG and the taste response can be understood and analyzed by a transduction model wherein the cellular depolarizations accompanying electrolyte fluxes through taste receptor cells provide the signal for the taste response.

The electrogustograph of the present invention has five major subassemblies plus a source of vacuum. These are the sensor subassembly, the isolated sensor amplifier and current source subassembly, the voltage/current clamp subassembly, the control subassembly and the fluid circulator subassembly.

The sensor is a small unit preferably ¾ inches in outside dimensions by ⅜th inches tall. Obviously, it can be of other sizes down to a size that accommodates a single papilla. From one side of the sensor assembly there are five ports, one for source of vacuum, one for a source of tastant fluid, one for a return of the tastant fluid, one for the insertion of a current electrode and one for the insertion of a voltage electrode. At the bottom of the assembly, which is a relatively flat surface there are two concentric rings approximately one millimeter in height. The inside diameter of the smaller ring is approximately ⅜th inch and defines a cavity, approximately 1 millimeter in height. The spacing between the two rings is approximately 1.5 millimeters in width. The annular space between the two rings has conduits in the bottom or housing of the sensor connecting the annular recess space with a vacuum so that when the sensor is placed on the tongue or other surface, it is attached by the vacuum which is preferably between 60 and 70 millimeters of mercury in negative pressure. This pressure would vary with the size of the ring, the nature of the surface to which it is attached and so forth.

In the central cavity or fluid receiving recess, there are three ports, a central port which is connected by a conduit within the body or housing of the sensor to the fluid inlet. The tastant fluid flows into the cavity through this port and across the surface of the tongue or other flexible surface to which the sensor is attached. The other two ports are on each side of the central port and one is used as a voltage electrode port and the other as a current electrode port. Near the outer periphery of the cavity is an annular port for the return of the tastant fluid. This port is connected by a conduit or passageway within the body or housing of the sensor to the fluid return port on the outside wall of the sensor. Other electrodes are placed on the outside of the cheeks when the test animal is a human being. This location is surprising as it actually works better than placing such electrodes, which are used to complete the electrical circuit, underneath the tongue opposite from the location where the sensor is vacuum attached or alternatively, on the sides of the tongue.

For safety purposes, it is critical that a human being tested be isolated from the source of the electricity. To accomplish this, an isolation subassembly is provided preferably using optical isolators.

Another subassembly is for optionally clamping either the voltage or the current when taking the electrical response generated by various tastants. This is connected to the control subassembly which provides the overall control, sequencing and timing of the system with adjunctive devices (which are not shown) for monitoring the results, recording the results and printing out the results.

Another important aspect of the invention is the arrangement for the selection and sequencing and pump delivery of the various fluids utilized in carrying out various test procedures. Preferably, there are two banks or sets of reservoirs, each of which has a number of tastants or stimulus fluids therein as well as a diluting solution reservoir for modifying the tastants as desired. The stimulus or tastant reservoirs are connected to a stimulus selection valve which in turn is connected to a stimulus intensity pump. The pump is a positive displacement pump so that the control of the fluid can be exact and, preferably, is a gear type of pump. This pump is set at a rate that the tastant or stimulus is to be delivered to the sensor assembly through a sequencing valve. The sequencing valve determines which of the two banks of reservoirs of the stimulus or tastant fluids is to be utilized and is connected to both stimulus intensity pumps on one side and to a purge pump and a flow pump on the opposite side. This permits the sequencing valve to connect the flow pump to the stimulus intensity pump from which the tastant fluid is desired and at the same time connect the other stimulus intensity pump to a purge pump. As the tastant is being delivered to the sensor from one reservoir and just prior to switching tastants, the other stimulus intensity pump and purge pump are activated to deliver the next selected tastant through the conduits, valves, stimulus intensity pump, purge pump and into a waste receptacle so that the lines will be clean of previous tastant and ready for the next tastant. This also eliminates any inertia in the system since the pumps are already running at the time the switchover take effect.

Located between the stimulus intensity pumps and sequencing valve is a branch conduit leading to a dilution or modifying solution reservoir.

The flow pump is also a positive displacement pump which preferably is of the gear type and it is designed to run at the same or a higher rate of throughput than the intensity pump. The difference in throughput of the flow pump and intensity pump withdraws diluting or modifying solution from the reservoir so as to dilute the tastant to a predetermined desired amount.

For better understanding of the invention, reference is made to the following description of an exemplary embodiment, taken in conjunction with the accompanying drawings.

Figure 8:
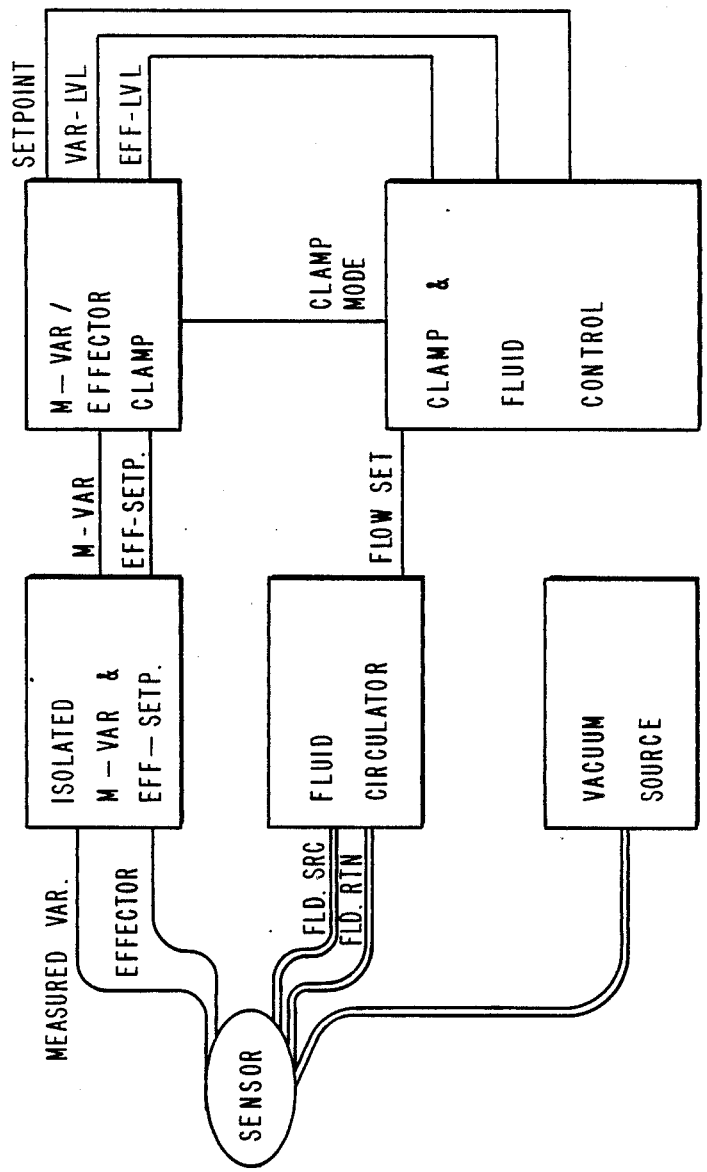
FIG. 8 is a broad schematic of the basic aspects of the invention.

With reference to FIG. 8, there is shown the electrogustograph in a broad schematic of the systems highest abstraction. First there is a sensor which is connected to a vacuum source for connecting the sensor to a flexible surface such as a skin or tongue. It is also connected to a fluid circulator which is connected to the sensor by a conduit supplying the fluid or fluid source (Fld.src) and another conduit which returns the fluid from the sensor (Fld.rtn). The fluid is a fluid used in a test such as a tastant.

Figure 9:
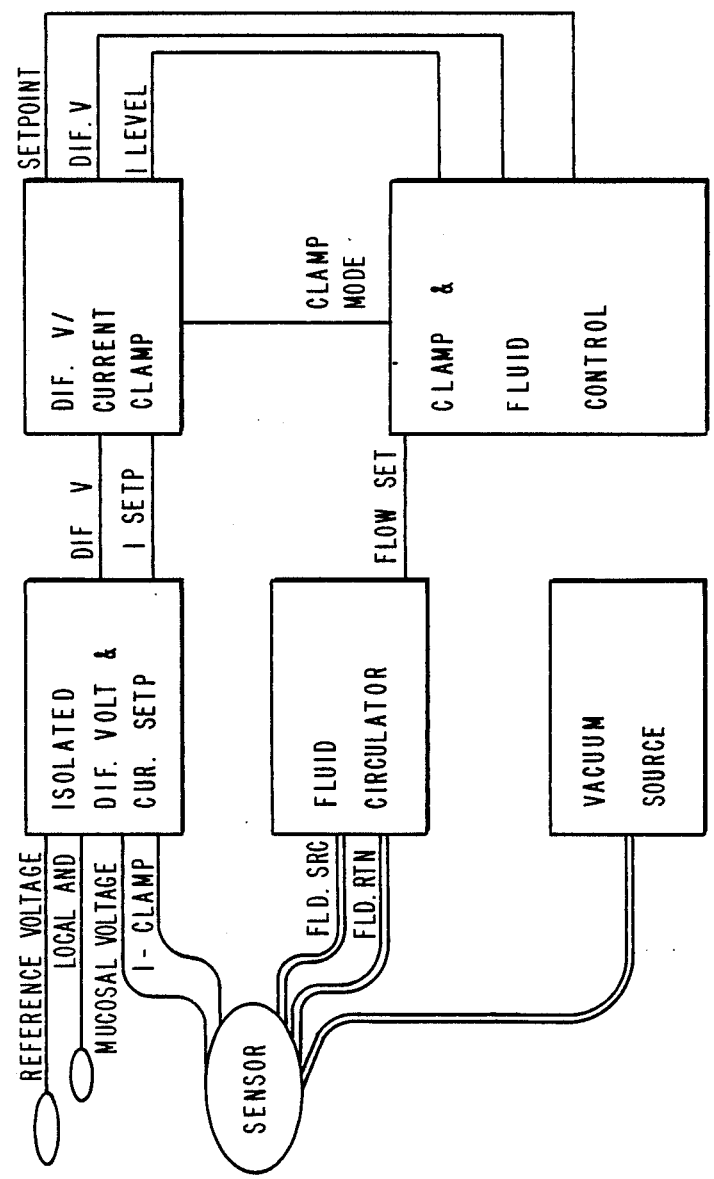
FIG. 9 is another broad schematic similar to FIG. 8 but with more specifics.

To determine the effect of the fluid, the sensor is also connected by two electric lines to the isolated measured variable (isolated M-Var) and the effector set point (Eff-setp). As is seen with reference to FIG. 9, which is similar to the broad schematic of FIG. 8 except it is more specific with regard to some of the features, the measured variable is the differential voltage and the effector setpoint is the current setpoint. Also as shown in FIG. 9, there is a reference voltage and local ground (gnd) mucosal voltage. The measured variable or differential voltage and effector or current set point are isolated preferably by optical isolation so that no electric currents at a dangerous level are connected to the person or animal being monitored. The measured variable in the case of FIG. 9 is the differential voltage (dif V) and the effector set point in the case of FIG. 9 is the current set point both of which are connected to a measured variable/effector clamp which is in effect a controller which allows the apparatus to clamp either the measured variable or the effector set point so that one can be treated as the independent variable and the other as a dependent variable. This is switched from one mode into another by a signal coming from the clamp and fluid control using the clamp mode connection. In other words, it switches from clamping the measured variable to clamping the effector variable. The three signals between the clamp and fluid control and the measured variable/effector clamp or, in the case of FIG. 9, the differential voltage/current clamp, are two signals coming from the measured variable/effector clamp which are the variable level (Var-lvl) and the effector level (Eff-lvl) and one signal going to the measured variable/effector clamp which is the set point. The set point is in effect the target level that is being clamped. One of the two signals, either the variable level or the effector level, will be exactly equal to the set point level dependent on the mode of the clamp. In the case of FIG. 9, the variable level is a differential voltage level and the effector level is the current level. Also, coming from the clamp and fluid control is a flow set to a fluid circulator. The flow set is a generalized signal and not a single signal. It controls the fluid flow pump and the fluid circulator in terms of the feed of the fluid from what ever source is selected. It permits the selection of whatever is going into the sensor and controls the fluid that is returned from the sensor.

Figure 1:
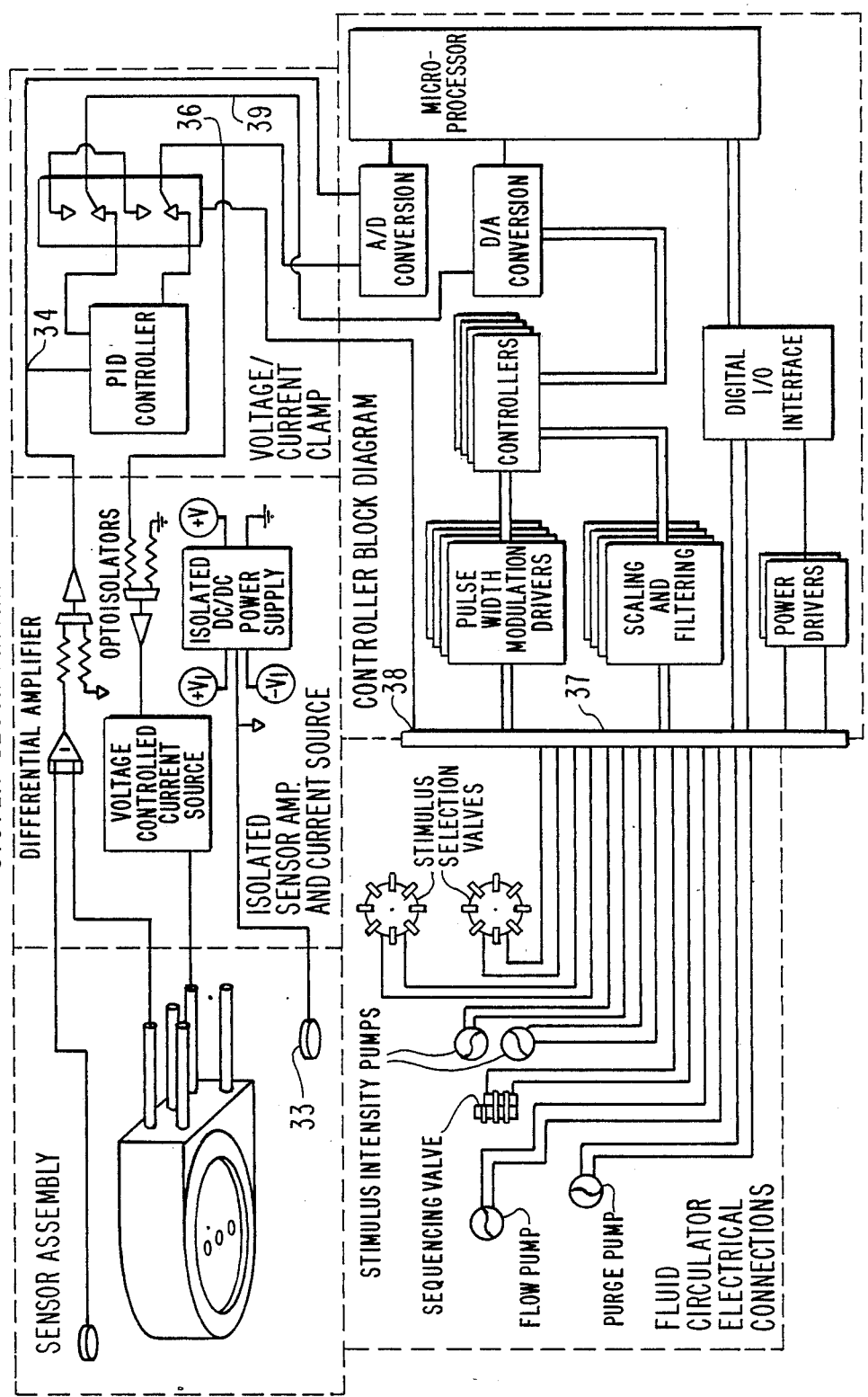
FIG. 1 is a block schematic of the electrogustograph of this invention.
Figure 2:
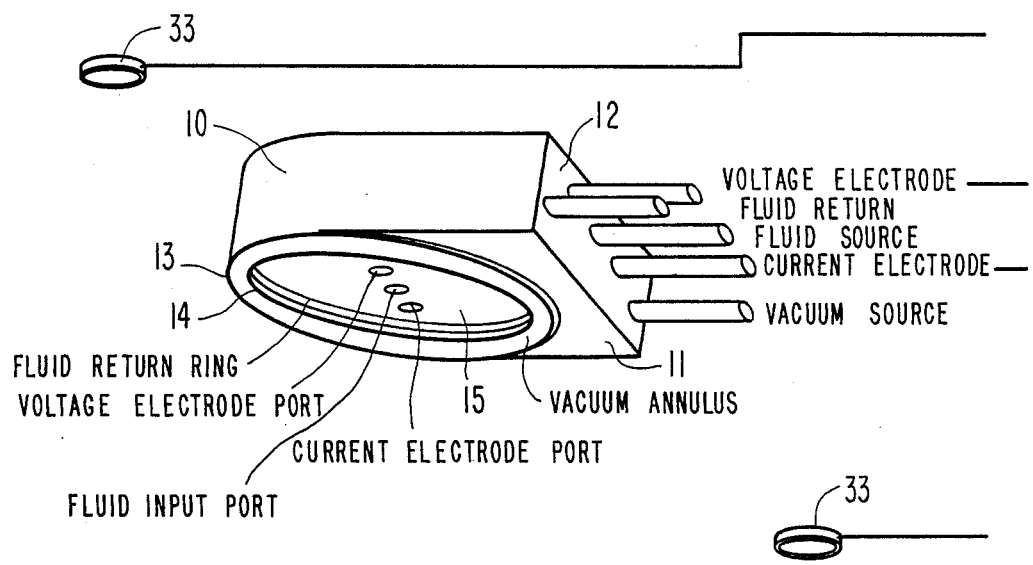
FIG. 2 is an enlarged perspective schematic of the sensor assembly of FIG. 1.
Figure 10:
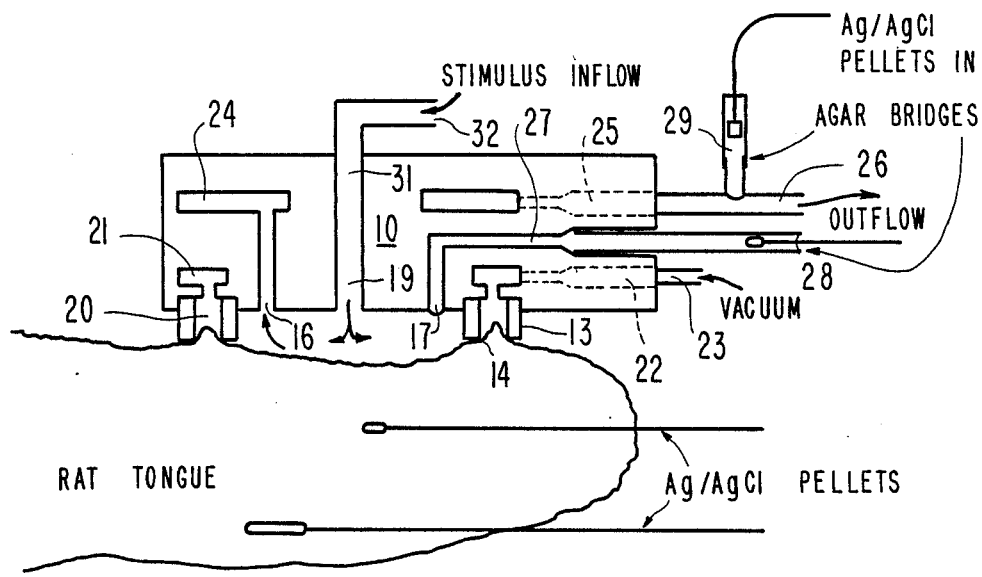
FIG. 10 is a schematic cross-section showing the application of the invention to a tongue.

With reference to FIG. 1, there is shown a system block diagram with five subsystems. The subsystems are the sensor assembly, the isolated sensor amplifier and current source, the voltage/current clamp, the controller block and the fluid circulator electrical connections. Each of these subsystems are shown in more detail in FIGS. 2-6. With reference to the sensor assembly, as shown in FIG. 2, there is a sensor housing or body 10 which has an attachment or underside 11 and a ported side 12. The preferred dimensions for this sensor body is ¾th inch outside diameter or width by ⅜th inch in height and is made of plastic. On the attachment side, there are two concentric rings, the outer ring or ridge 13 and the inner ring or ridge 14. Preferably, these ridges are 1 millimeter in height. The vacuum annulus or annular recess space between these two ridges has a width of approximately 1.5 millimeters. The area on the attachment side of the body within the inner concentric ring 14 is a cavity or fluid receiving recess 15 for receiving the fluid. This cavity is 1 millimeter in depth and has four ports. The first port is an annular fluid return ring 16. The other ports are a voltage electrode ports and a current electrode port and in the center is the fluid input port. All of these ports are connected by conduits or passageways in the sensor housing or body and are connected to side ports on the ported side 12. These side ports are a voltage electrode port, a fluid return port, a fluid source port, a current electrode port and a vacuum source. The internal porting is shown in a highly schematized fashion in FIG. 10 where the vacuum sensor body is attached by vacuum to a rat tongue. As seen in FIG. 10, the vacuum annulus port 20 is connected to an inner annular cavity 21 which leads to a conduit 22 that exits at the vacuum port 23. The annular fluid return ring port 16 (only partially shown in FIG. 10) has a conduit connecting it to an annular ring cavity 24 which is connected to a conduit 25 that leads to the fluid return or outflow port 26.

The voltage electrode port 17 is connected by a conduit 27 to a voltage electrode port 28 into which a voltage electrode is inserted. The current electrode port is not shown in FIG. 10 but would have a similar internal conduit connected to the current electrode port in the ported wall of the sensor housing as was the voltage electrode port. In FIG. 10, an optional arrangement is used whereby the current electrode is inserted in a branch conduit 29 that branches off the fluid return outlet port 26. The fluid input port 19 is connected by a conduit 31 to a stimulus inflow or fluid source port 32.

In FIG. 2, this fluid source port does not come out of the top of the body but instead comes out of a ported side of the sensor body or housing. The preferred arrangement is that shown in FIG. 2 and FIG. 10 is primarily to show in a highly schematized form the application of the sensor to the flat flexible surface of a rat tongue.

The two electrodes are preferably of the silver/silver chloride pellet types and are inserted into the sensor body or housing by agar bridges as shown in FIG. 10. Two other electrodes using silver/silver chloride pellet electrodes are attached to the side or underside of the rat's tongue. In the case of FIG. 2, these external electrodes 33 are preferably placed on the outside cheek of humans when humans are being tested.

The sensor can be made smaller than the one mentioned above and even down to a size where the cavity is only approximately 11/78 to 2 millimeters in diameter. At this size, the cavity would probably cover only one papilla and the remainder of the sensor would be sized accordingly.

The positive displacement pumps used to supply fluid to the cavity preferably pump at a flow rate from 0.1 to 1.0 ml/sec.

One of the big problems is that the dynamic range of the positive displacement gear pumps which vary the gross flow rate over a 200 to 1 range. This dynamic range problem has been solved in a manner that will be described later. While the flow rate may seem small, the fluid cavity is quite small so the change of fluid is frequent.

The electrodes which are separate from the sensor body or housing are, surprisingly, successful applied to the outside of the cheeks. One of these is simply a voltage sensing electrode and senses the voltage potential present on the body. It works on the cheek without picking up any particular interfering type of signals. While intuitively it would seem it would be best if the electrode was physically close to the electrode in the sensor body, such as underneath the tongue it is not as satisfactory in that location. While it works, it is uncomfortable and there are other problems associated with that location such as the potentials which are generated when the tongue muscle is exercised. The reason that it works on the outside of the cheek is that the epithelial sheet that the voltage is being measured across is much higher in resistance than the bulk of the fluid systems between the tongue and the rest of the body. Therefore, there is very little error in applying it to the cheek. That location also picks up fewer tongue movement artifacts. Those potentials generated simply by the tongue muscle activity seem to be rejected by putting the external electrode on the cheek.

The vacuum draw on the vacuum annulus port is preferably 50 to 70 millimeters of negative mercury pressure. This can be varied when the size of the sensor and the type of flexible surface it is being applied to are varied.

While the sensor is preferably applied to the top of the tongue in the case of the electrogustograph, it can also be applied on the inside of the cheek or on the palate. It can also be applied to other flexible surfaces when a physiological response is being tested with various test fluids. For example, it may be used on the skin with reference to sweat glands to determine the electrical activities which are occurring. This may indicate a state of stress.

Potential applications other than those already mentioned include a measurement of sweat glands for diseases and possible studies of changes in the sweat glands associated with cystic fibrosis.

While electrodes are the preferred choice for receiving the measurements, other types of detectors could be used such as measuring the metabolic properties represented by the thermal response of tissue using temperature detectors. Also, ion selective electrodes and pH electrodes can be utilized to pick up changes in the composition of saliva at the time the different presentations of stimulating fluids.

The primary measurement in the electrogustograph is the measuring of the changes in potential between the inside of the fluid chamber to the cheek when various tastants are applied to the tongue in the cavity. Surprisingly, few stray currents or jump spikes have interfered with the measurements.

Figure 3:
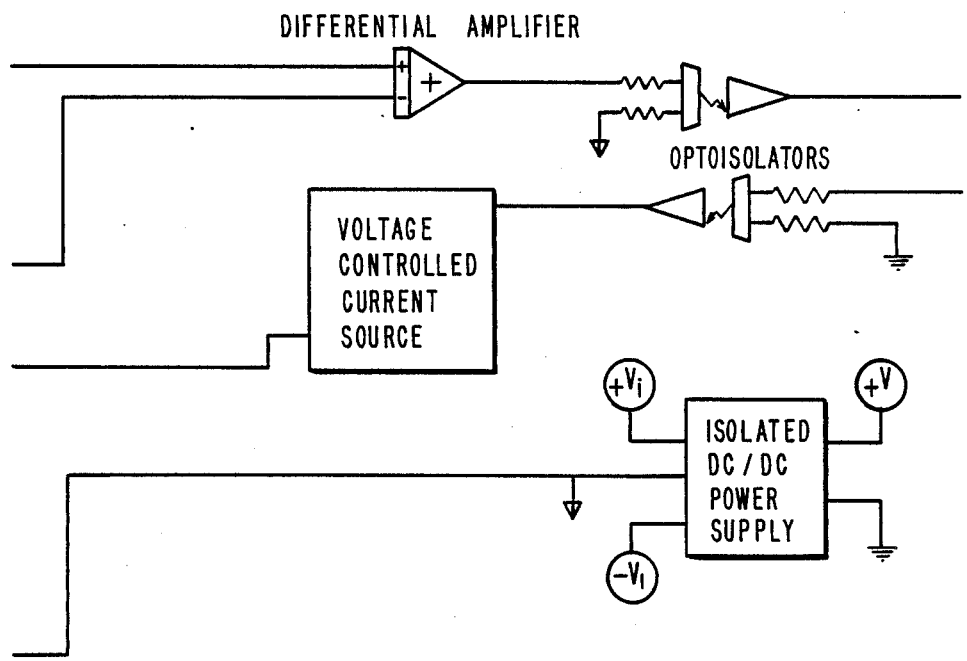
FIG. 3 is an enlarged schematic of the isolated sensor amplifier and current source of FIG. 1.

With reference to FIG. 3, there is shown a circuit for isolating the source of the electric current from the sensor which is necessary for safety purposes when measurements are being made with human beings. The preferred type of isolation is optical isolation by separating the differential amplifier and the voltage control current source from the source of electricity. Also, the isolated DC/DC power supply which is connected to the remaining external electrode 33.

The differential amplifier is used to measure the difference between the electrode which is in contact with the fluid inside the fluid chamber of the sensor housing and that potential which is present at the cheek where the other reference electrode is applied. This is the measured variable.

The voltage controlled current source is a standard type of electrical device that measures the current and forces it to a specific level. This is the effector variable.

Figure 4:
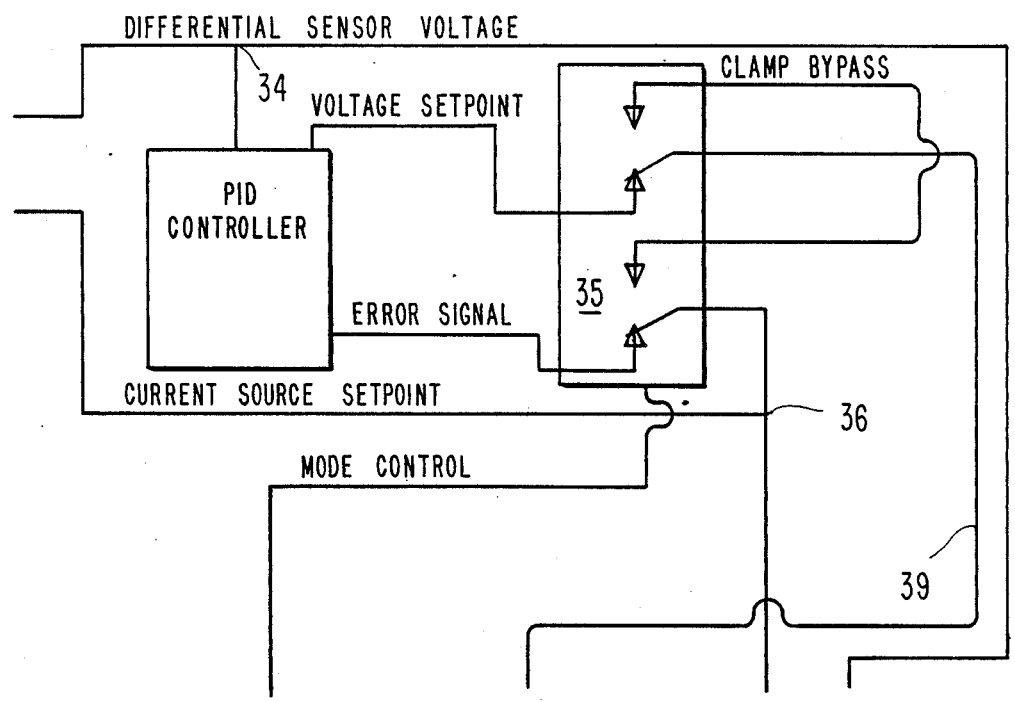
FIG. 4 is an enlarged schematic of the voltage/current clamp of FIG. 1.

With reference to FIG. 4, there is shown a voltage/current clamp which uses a proportional, integral and differential (PID) controller as is well known in process control. It taps onto the differential sensor voltage line at 34 and is connected by a voltage setpoint line and an error signal line to the switches in switching box 35.

A current source setpoint line is connected between the optoisolator for the voltage controlled current source to the line running between the switching box 35 and the A/D conversion at junction 36. A clamp bypass runs between the two switches or relays in the switching box 35. A mode control line runs from the switching box 35 to connect to bus 37 at 38. A line 39 for clamp setpoint connects switch or relay in switching box 35 to the D/A conversion.

The switching box 35 is simply a voltage control switch which may be a relay or a semiconductor switching device. In the voltage clamp mode, it switches the PID controller into the circuit. In the current clamp mode, it switches the PID controller out of the circuit. When the PID controller is switched out of the circuit the set point which comes into it is transmitted directly to the voltage controlled current source and that in itself clamps the current to a specified level. Only when the voltage is being clamped is the PID controller actually being utilized.

Generally, it has been found more desirable to operate in the current clamp mode.

Figure 5:
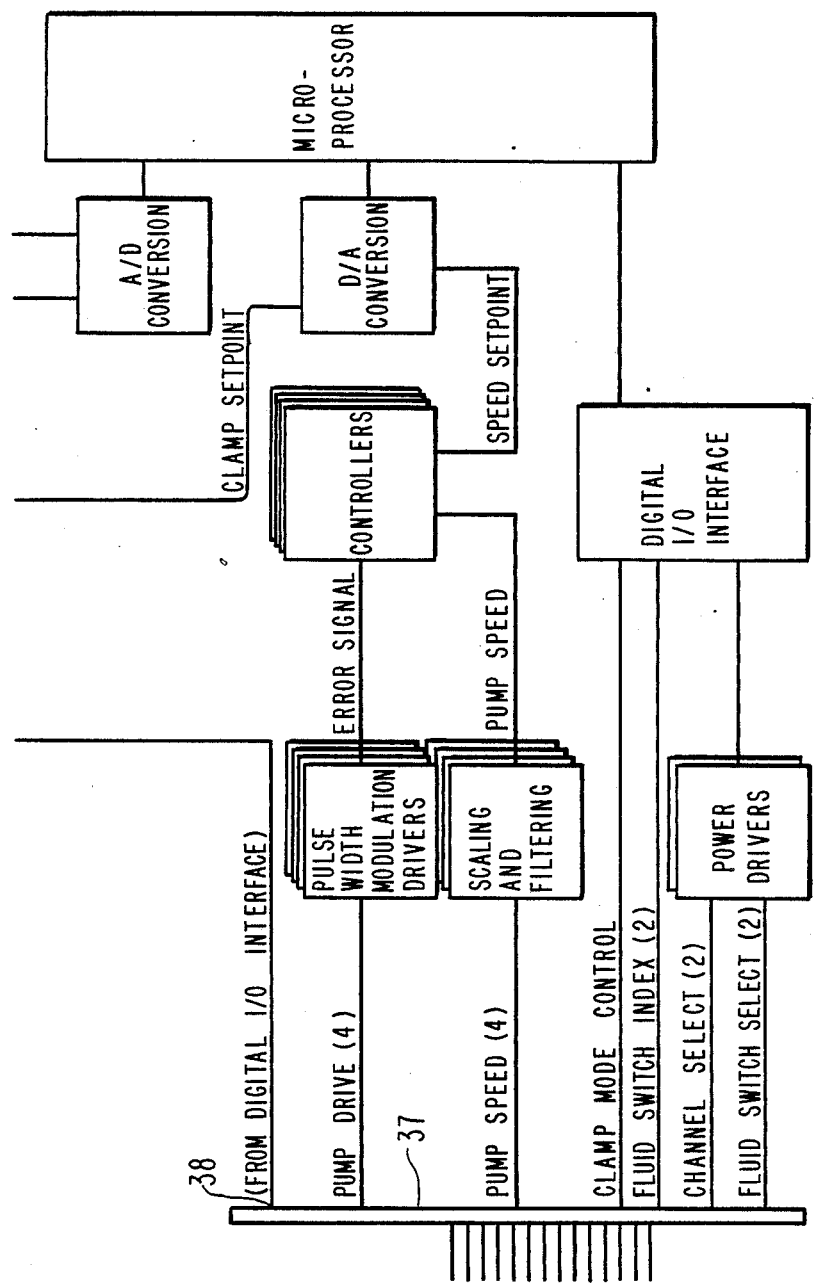
FIG. 5 is an enlarged schematic of the controller block diagram of FIG. 1.

With reference FIG. 5, there is shown the controller block diagram. This is where the major controlling functions occur under the control of a microprocessor which performs all of the controlling functions required by the system such as the sequencing of the pumps, valve selection, pump speed control, clamp set points and the like. Not shown, in the controller block diagram are the obvious and well known components of a small microcomputer including a Winchester hard disk for memory, a recorder, and a printer.

The various signals received from the voltage/current clamp subassembly are analog signals which are converted to digital signals before being inserted into the microprocessor. This is done by the A/D conversion. The output from the microprocessor is converted from digital to analog before being fed back into the voltage/current clamp subassembly or subsystem and to the controllers. Also the microprocessor is connected to the microcomputer which is not shown. The four controllers are analog type of controllers and are the proportional, integral and differential (PID) type of controller. There is one controller for each of the pumps.

A signal from the microprocessor is sent to the controllers to represent a pump rate and the controller is in a closed loop feedback system with optical encoders on the shaft of the pumps. The optical encoders used are a standard type of sine-cosine optical encoder preferably those manufactured by Sharp as Model Nos. GEA94HV. Such encoders are available from a number of sources.

The feedback signal from the optical encoders is in the form of a sine-cosine signal that is filtered and scaled to convert it to a DC signal which is fed into the controller. The controller compares this DC voltage signal with the reference voltage and generates an error voltage to change the duration of the pulses of the pulse width modulation drivers.

The electric motors driving the pumps are controlled as to speed by the pulse width modulation drivers. The motor for each of the four pumps has a dedicated pulse width modulation driver as well as a scaling and filtering circuit.

The power drivers are utilized to take the low logic level signals from the microprocessor, which signal level is insufficient in itself to operate various switches to the pumps and solenoids and converts them to voltage and current levels sufficient to operate such switches and solenoids. The power drivers are connected to the microprocessor through the digital input-/output (I/0) interface. The digital I/0 interface also is connected directly to the bus 37 which has the function of intermingling the various signals going into and out of the bus structure. The digital I/0 interface also connects the microprocessor to the stimuli selection valves and sequencing valves as will be discussed in connection with FIGS. 6 and 7.

Figure 6:
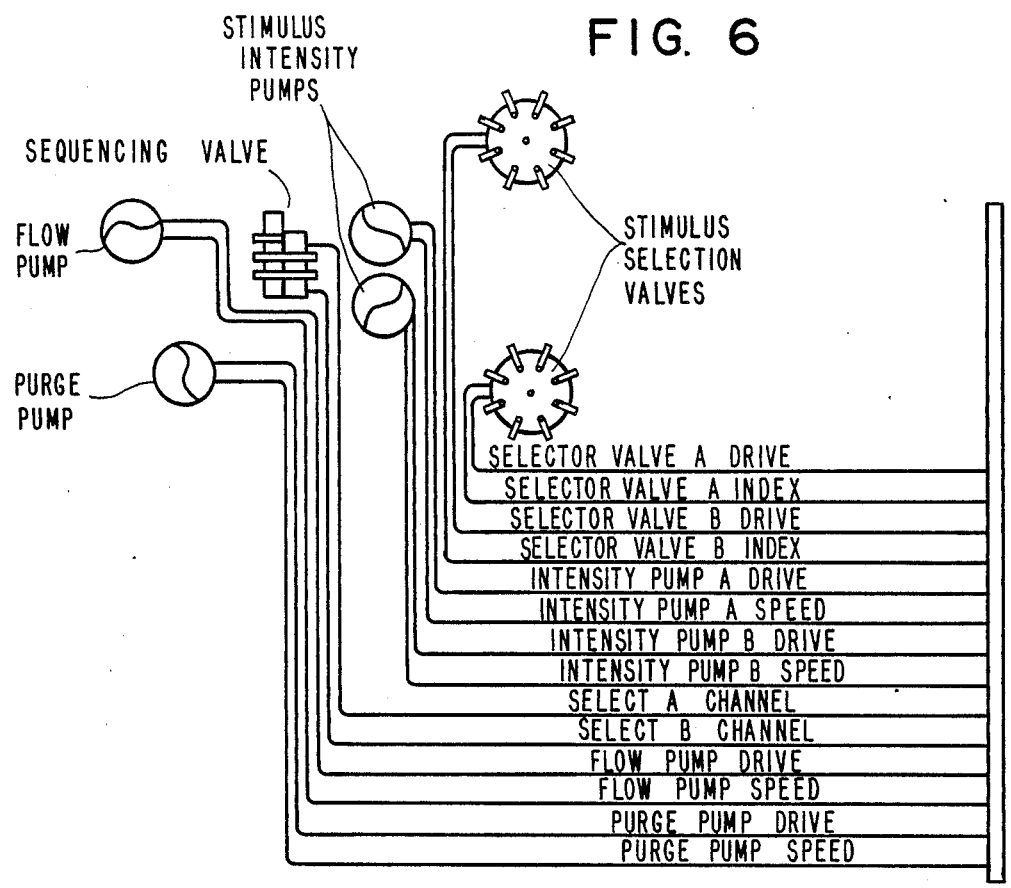
FIG. 6 is an enlarged schematic of the fluid circulator electrical connections of FIG. 1.
Figure 7:
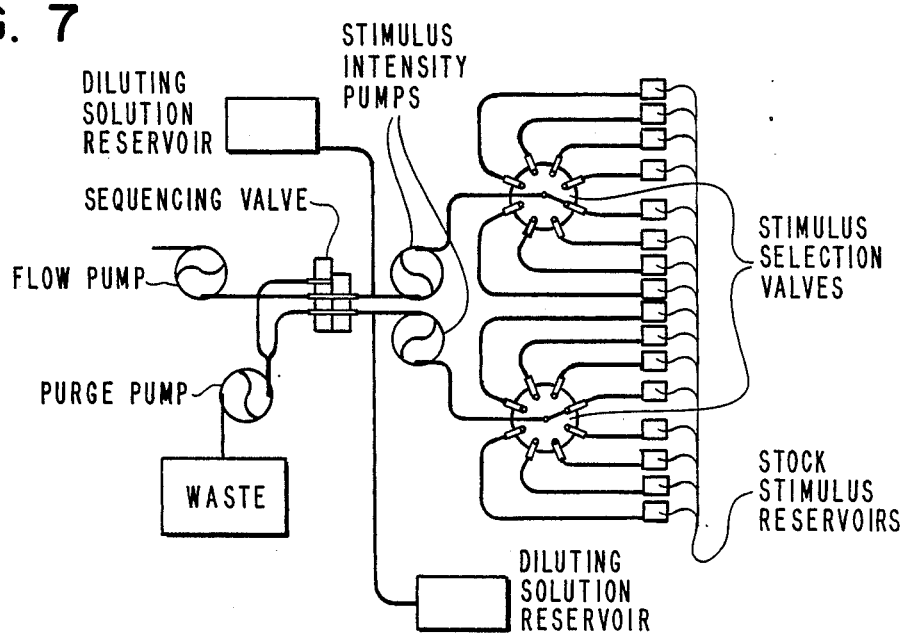
FIG. 7 is a fluid flow diagram of the invention similar to FIG. 6.

With reference to FIGS. 6 and 7, they show respectively the fluid circulator electrical connections and the system for handling the various fluids. FIG. 7 shows two sets or banks of of stock stimulus reservoirs for containing the test or tastant fluids. Each of these sets of reservoirs go to a pancake sequence selection valve which is connected to a stimulus intensity pump. Both stimulus intensity pumps are connected to a sliding sequencing valve which is connected directly to a flow pump and to a purge pump. The purge pump dumps its fluid into a waste reservoir.

Each set or bank of stock stimulus reservoirs has associated therewith a diluting or modifying solution reservoir which is connected by conduit to the conduit running between the stimulus intensity pump and the sequencing valve.

The four pumps are positive displacement pumps so that the rate of fluid flow can be accurately controlled. Preferably gear pumps are utilized.

The shaft of each of the gear pumps has a sine-cosine optical encoder (not shown) so that a feedback to the respective controller for each of the pumps can provide better control. The speed of the pumps are under the control of the controller and is determined by the width of the pulses coming from the pulse width modulation driver associated with each pump.

The stimulus selection valves are run by DC motors having a shaft encoder which sends two logic level signals back, one being an index pulse which shows when the stepping motor has completed one revolution and the other being a signal for each step. This functions as a form of crude stepping motor and serves to position the pancake stimulus selection valves to access a selected stock stimulus reservoir. This is done through the digital I/0 interface. There are numerous well known ways by which selecting the proper stimulus reservoir can be made.

With reference to FIG. 6, the upper stimulus selection valve, stimulus intensity pump and conduits associated therewith are referred to as "valve b", "pump b" and "b channel". The lower selector valve, intensity pump, and associated conduits are referred to as "valve a", "pump a" and "a channel". The control signals coming from the controller subassembly determines the selector valves "a" and "b" drive and index, determines the intensity pumps "a" and "b" drive and speed, selects either the "a" or "b" channel and determines the flow pump and purge pump drive and speed.

The sequencing valve is a slider valve driven by a solenoid but numerous other well known valves can be utilized to provide the function. In operation, either the "a" set or "b" set of stock stimulus reservoirs are selected by the sequencing valve and one of the eight stock stimulus reservoirs of the selected set is selected by the stimulus selection valve.

The stimulus intensity pump associated with the stimulus selection valve is driven at a predetermined rate to withdraw fluid from the selected reservoir which is caused to flow to the sequencing valve and then to the flow pump. The flow pump is driven at a predetermined rate which is the same rate or higher as the throughput rate of the stimulus intensity pump. Any differential between the rates serves to withdraw fluid from the diluting or modifying solution reservoir to modify or dilute the stock stimulus fluid. The fluid then flows to the sensor assembly where it is passed over the surface of the tongue and is returned to be dumped. At the same time, the sequencing valve has connected the purge pump to a waste container and to the idle stimulus intensity pump.

During use, the purge pump is inactive until it is desired to test with a different stimulus fluid. When this occurs, the next stock stimulus fluid to be used is selected by the stimulus selection valve and the associated stimulus intensity pump and the purge pump are activated to run the next stock stimulus fluid through the pump sequencing valve, conduits and stimulus intensity pump to purge them of any other fluid that may be left therein and also prime the conduits, stimulus intensity pump and selection valves with the new fluid and get the pumps running prior to the switch over to the new fluid to be tested. This activation takes place just prior to the switch over and eliminates much of the inertia in the system.

The four pumps have a very large dynamic range which may be from 1 to 200 which creates a control problem. To accurately control such a dynamic range, the inventors have created a new control implementation. The sine-cosine signal coming from the optical encoder associated with a given pump, instead of simply being rectified and averaged, as has been done in the past, is processed as follows. The sine signal is differentiated and changed to a cosine. In the process of differentiating, there is developed a coefficient which is proportional to frequency. This derived cosine signal is multiplied by the cosine signal. The resulting cosine squared signal also has a coefficient which is proportional to frequency. This is done also with the cosine signal which is differentiated to give a sine signal with a coefficient which is proportional to a frequency. This is multiplied by the sine signal. With the differentiating network being the same in both instances, the coefficient for both sides is the same, so when the sine squared plus cosine squared signal is summed, there is present a constant voltage signal which has a coefficient which is proportional to frequency. This procedure represents a demodulation scheme which is valid over wide range of frequencies and has a very low ripple. This is especially helpful because the pumps are sometimes run at very slow speeds and yet need a good dynamic response.

A more conventional control strategy would be to rectify and filter the AC signal from the optical encoder to obtain a DC speed signal. Lowpass filters with time constants large enough to remove ripple at low frequencies would limit the dynamic response of the pump.

When the invention is used for salt testing, usually a solution of ten millimolar salt solution (the salt being referred to is sodium chloride or table salt) is used to flush the chamber or fluid receiving recess in the sensor for approximately 1 minute. Next, there is a series of applications of a solution of a stimulus fluid that is of increasing sodium chloride concentration. For example, in using the ten millimolar sodium chloride to flush, the next step would be to put a 50 millimolar sodium chloride solution through the chamber and then observe the deflection of the instruments indicating the electrical change. This would again be done for approximately 1 minute and up to 5 minutes depending on how the particular tongue is responding to this solution. The length of time is usually determined by the time it takes to reach a relatively steady state condition.

The sodium chloride stimulus generally evokes an initial fast inward current and conductance increase followed by a slow inward current and a slow conductant increase. These currents and conductance changes coincide respectively with the rising phase and adaptation phase of the neural response. It has been determined in the experiments that the rate of decline is much lower than was previously thought.

It is not essential in all instances to await attaining a steady state condition.

After a selected test concentration is utilized, the tongue surface is purged with a reference solution of sodium chloride of 10 millimolar concentration.

As background, the normal concentration in saliva is between 30 to 100 millimolar and the concentration in the blood stream is 150 millimolar. Therefore, a 150 millimolar saline solution is comparable to what is found in a bloodstream. The concentrations are continuously increased in carrying out the experiments by next testing a 100 millimolar solution of sodium chloride followed by flushing of the surface of the tongue with the 10 millimolar solution. This is followed by using a 150 millimolar solution of sodium chloride. This can proceed on up to a 2 molar solution which is of course quite salty.

Figure 11:
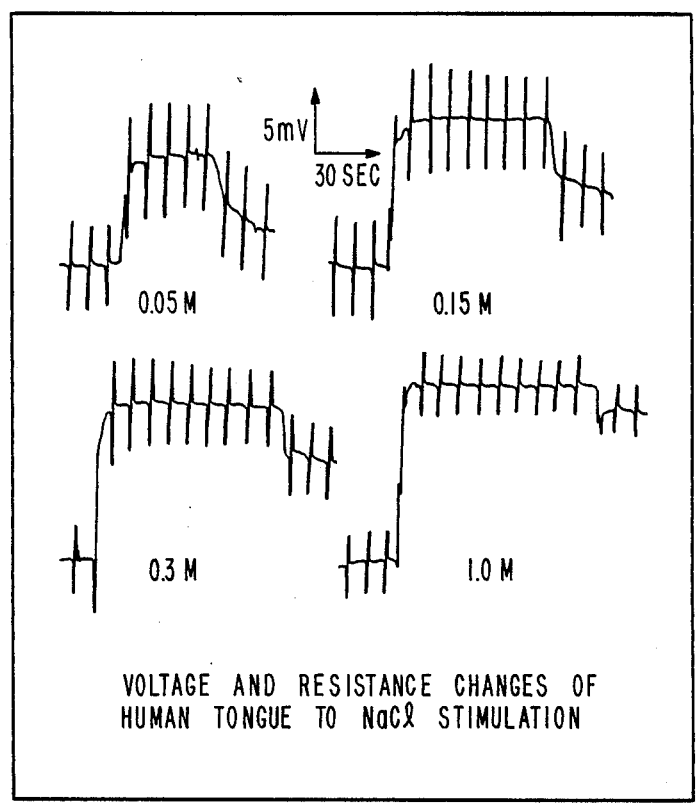
FIG. 11 is a chart showing the voltage and resistance changes on the human tongue in response to NaCl stimulation.

FIGS. 11-15 show various response curves with different solutions being testing. FIG. 11 shows the voltage and resistance changes of the human tongue to sodium chloride stimulation under four different concentrations. The concentrations are 0.05 molar, 0.15 molar, 0.3 molar and 1.0 molar. There is shown a relative scale of the millivolts and time which can be used in interpreting the readings. As is seen in the four curves, there is an initial jump in the voltage level followed by an adaptation decline to the right of the curves.

The curves consist of various spikes and relatively horizontal lines between the spikes. These horizontal lines in effect show the open circuit voltage response which consist of a voltage change from a base line value and are believed to be asymptotic to a new pseudo steady state value. Two measures can be used in interpreting the curves. One is the open circuit voltage changes and the other is the peak-to-peak deviation in response to the pulses.

Figure 12:
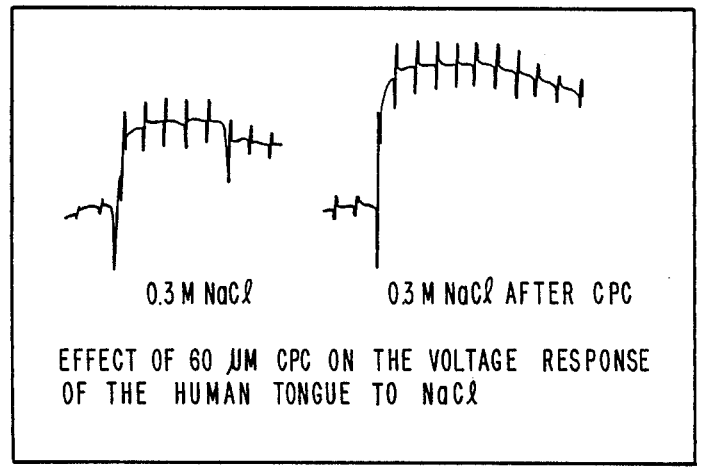
FIG. 12 is a chart showing the voltage response when NaCl and CPC are applied to a human tongue.

FIG. 12 shows the effect of introducing 60 micromolar concentration of CPC on the voltage response of the human tongue to sodium chloride. The first curve shows a 0.3 molar concentration of sodium chloride without any CPC and the second shows the same concentration of sodium chloride with the 60 micromolar concentration of CPC added. This curve indicates a much stronger response as to salt taste than the first curve. These curves were generated in connection with the inventors' invention of a salt taste enhancer, the preferred composition of which is the cationic surfactant cetylpyridinium chloride (CPC).

Figure 13:
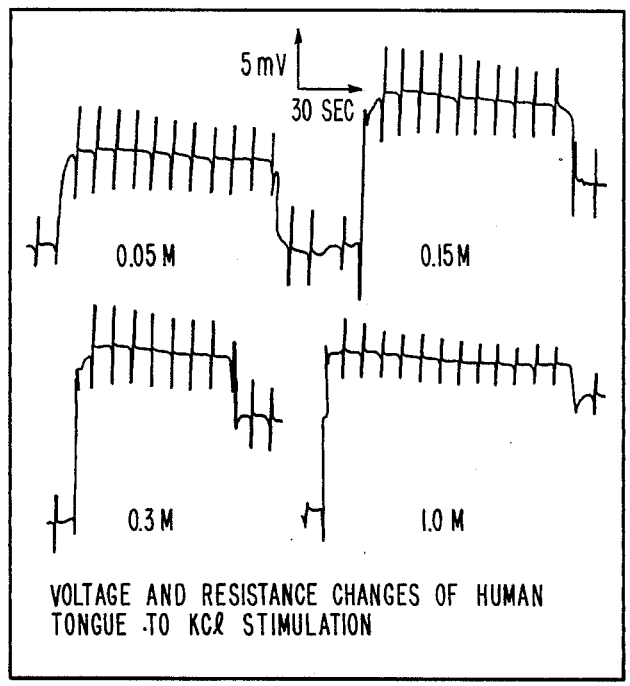
FIG. 13 shows changes of voltage and resistance when KCl is applied to a human tongue.
Figure 14:
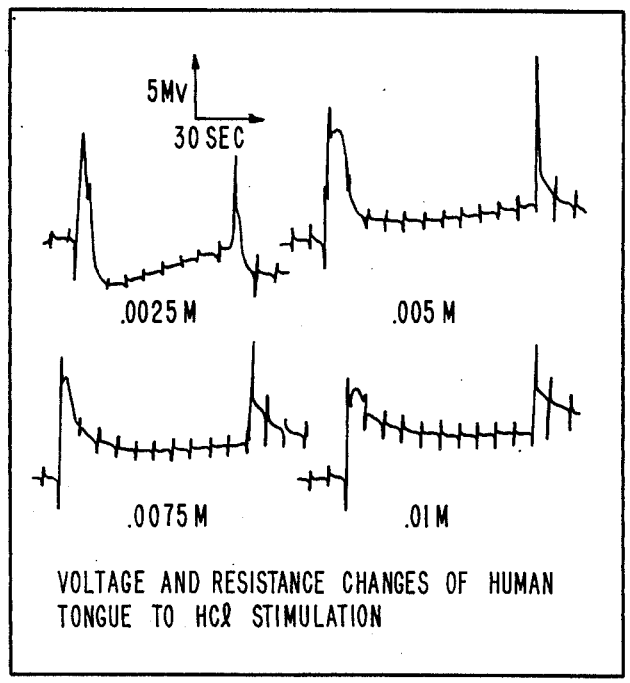
FIG. 14 shows changes of voltage and resistance when HCl is applied to a human tongue.

With reference to FIG. 13, there are four curves showing the voltage and resistance changes of the human tongue to potassium chloride stimulation. The first curve is a 0.05 molar solution, the second curve a 0.15 molar solution, the third curve a 0.3 molar solution and the fourth curve a 1.0 molar solution. In general, FIG. 13 shows that the potassium stimulation produces the same kind of jumps obtained with sodium chloride but they come back to a different base line. The indication is that the potassium chloride can be differentiated from sodium chloride on the basis of dynamics and the time constants which can be measured in the responses. With reference to FIG. 14, there is shown four curves of varying concentrations of the voltage and resistance changes of the human tongue to hydrochloric acid stimulation. This in effect represents a sour taste. The concentrations are 0.0025 molar, 0.005 molar, 0.0075 molar and 0.01 molar.

Figure 15:
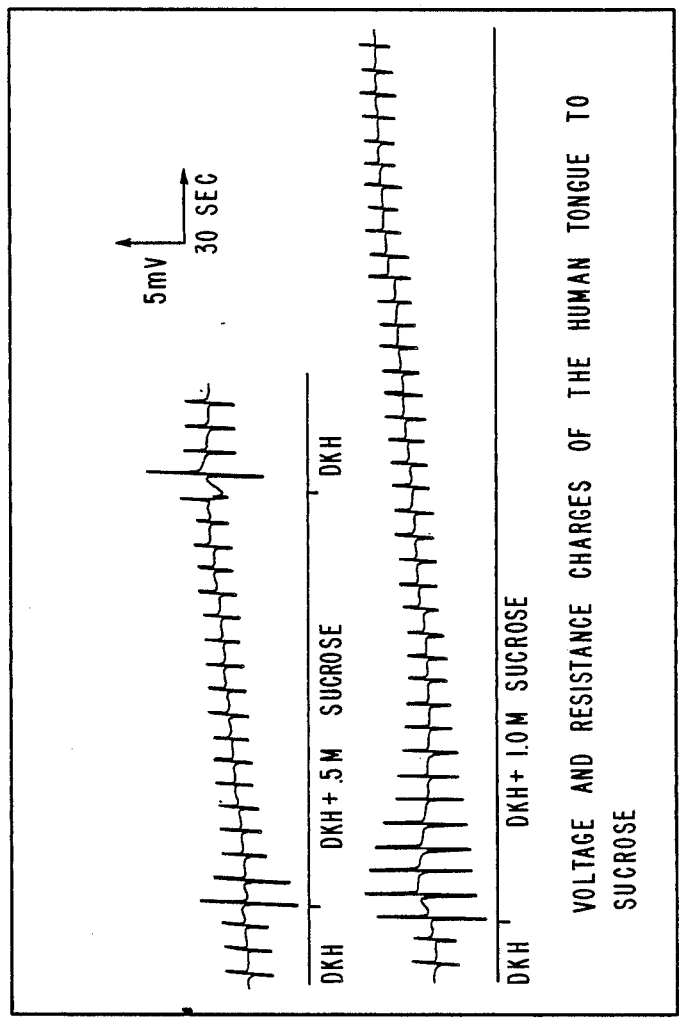
FIG. 15 shows voltage and resistance changes when DKH and sucrose are applied to a human tongue.

FIG. 15 shows the voltage and resistance changes of the human tongue to sucrose which is a measure of the sweet taste. The first curve is DKH alone followed by DKH plus a 0.5 molar concentration of sucrose followed by DKH alone. The second curve is DKH alone followed by DKH plus 1.0 molar concentration of sucrose.

DKH is a saliva substitute. The KH portion is the well known mammalian buffer which is designed to match the blood levels of electrolytes in mammals. In its expanded form, it is Krebs-Henselheit. The "D" stands for "depleted" which means that sodium has been depleted from the Krebs-Henselheit buffer. Not all the sodium is removed but only a portion.

There has thus been disclosed an electrogustograph which can be utilized not only as a highly flexible research instrument but the underlying concepts can also be used for other physiological testing.

If the electrogustograph is designed for a specific quality control function or other applications other than research it does not need the flexibility provided in the present instrument and can be greatly simplified. Also, it can be appreciated that instead of using a flow pump in series with a stimulus intensity pump, there can be provided a stimulus intensity pump by itself and a separate parallel pump, if needed, for the diluting or modifying solution.

Although the invention has been described in detail with reference to a certain preferred embodiment, it will be understood that variations and modifications may be made within the spirit and scope of the invention as defined in the appended claims.

What is claimed is:

1. A sensor for measuring a physiological response by attachment to the flexible surface of a living animal comprising:
- a housing having an outer wall with a first side for attachment to said flexible surface;
- an outer ring on said first side;
- an inner ring on said first side concentric with said outer ring and defining an annular recessed space between said rings;
- a fluid receiving recess on said first side within the boundary of said inner ring;
- a fluid inlet on said housing having a passageway connecting said inlet to said fluid receiving recess for receiving a fluid;
- a fluid outlet on said housing having a passageway connecting said outlet to said fluid receiving recess; and
- a vacuum inlet on said housing connected to said recessed annular space.

2. The sensor of claim 1 which includes a means on said housing for receiving a sensing device for detecting physiological changes when said housing is attached on said first side to said flexible surface and a fluid is caused to flow over a portion of said flexible surface adjacent said fluid receiving recess.

3. The sensor of claim 2 wherein said flexible surface is the upper surface of a tongue and said physiological response is the gustative response to liquids passed over the surface of the tongue wherein said sensing device receiving means on said housing includes a passageway in said housing which is in electrical communication with said fluid receiving recess when said recess contains a fluid therein.

4. The sensor of claim 3 wherein said housing includes a passageway between said fluid receiving recess and an electrode passageway port on said outer wall of said housing into which an electrode may be inserted.

5. The sensor of claim 4 which includes a passageway in said housing extending from said fluid outlet passageway to an external surface of said housing into which a second electrode may be inserted.

6. The sensor of claim 3 in which said housing is relatively flat with two opposite sides and an exterior side wall defining a thickness between said opposite sides and with said first side being one of said opposite sides and said fluid inlet, said fluid outlet, said vacuum inlet and said electrode passageway port are all in the same general vicinity on said exterior side wall.

7. A system for measuring a physiological response by attachment to the flexible surface of a living animal comprising:
- a sensor housing having an outer wall with a first side for attachment to said flexible surface;
- said sensor housing having an outer ring on said first side;
- said sensor housing having an inner ring on said first side concentric with said outer ring and defining an annular recessed space between said rings;
- said sensor housing having a fluid receiving recess on said first side within the boundary of said inner ring;
- a fluid inlet on said sensor housing having a passageway connecting said inlet to said fluid receiving recess for receiving a fluid;
- a fluid outlet on said sensor housing having a passageway connecting said outlet to said fluid receiving recess; and
- a vacuum inlet on said sensor housing connected to said recessed annular space;
- a reservoir for a stimulus fluid connected to said fluid inlet on said sensor housing; and
- a means for circulating a stimulus fluid from said reservoir to said fluid inlet at a predetermined rate.

8. The system of claim 7 wherein said system is an electrogustograph with said sensor housing designed to be attached to the upper surface of a tongue for sensing gustative responses to liquids passed over the surface of the tongue comprising:
- said sensor housing including a passageway between said fluid receiving recess and a electrode port on said outer wall of said sensor housing;
- a first electrode inserted into said electrode port;
- a source of electricity connected to said electrode;
- a second electrode for attachment to the animal being tested outside of the area of said flexible surface to which said fluid receiving recess would be attached to complete the electrical circuit between said first and said second electrodes when said sensor housing is attached to the test animal and fluid is present in said fluid receiving recess; and
- a source of vacuum connected to said vacuum inlet.

9. The system of claim 8 which includes an electrical isolation arrangement between said source of electricity and said first and second electrodes so as to isolate the test animal from any dangerous levels of electricity.

10. The system of claim 9 wherein said second electrode is adapted to be placed on the outside surface of an animals cheek and said sensor housing with said first electrode is attached to the upper surface of an animal's tongue when the test animal is a human being.

11. The system of claim 10 wherein there are a plurality of said reservoirs of stimulus fluids and said system includes selector valves for selecting which of said reservoirs is connected to said sensor housing.

12. The system of claim 11 which includes:
- a reservoir of modifying fluid for blending with the stimulus fluids contained in said stimulus fluid reservoirs and said circulating means is adapted to control the amount of modification by the modifying fluid of the fluid being circulated from the selected stimulus fluid reservoir.

13. The system of claim 12 wherein:
- said circulating means is a pumping arrangement which includes a first stimulus intensity pump connected to a first selector valve for pumping a selected stimulus fluid from said reservoirs at a predetermined rate;
- said pumping arrangement further including a floW, pump connected by a conduit to said stimulus intensity pump for pumping a fluid at a predetermined rate which is equal to or higher than the predetermined rate pumped by said stimulus intensity pump; and
- a conduit connecting said modifying fluid reservoir to said conduit between said stimulus intensity pump and said flow pump at a location between the two pumps whereby the difference in rate of pumping between the two pumps determines the amount of modifying fluid added to the selected fluid.

14. The system of claim 13 which includes:
- a second set of said stimulus fluid reservoirs, said modifying fluid reservoir, said selector valves, and said stimulus intensity pump; and
- a sequencing valve in said conduit between said flow pump and said first and second stimulus intensity pumps downstream from said connection to said modifying fluid reservoirs whereby either said first or said second stimulus intensity pump may be connected to said flow pump.

15. The system of claim 14 which includes:

a purge pump connected to said sequencing valve whereby the conduits leading to said stimulus pump and said stimulus pump which is not connected to said flow pump is connected to the next selection of a stimulus fluid and activated prior to switching to the next selection to surge the conduits and stimulus pump prior to being used for the next selection.

* * * * *